(12) United States Patent
Thede

(10) Patent No.: US 6,471,646 B1
(45) Date of Patent: Oct. 29, 2002

(54) ARTERIAL LINE EMULATOR

(75) Inventor: Roger C. Thede, Afton, MN (US)

(73) Assignee: Medwave, Inc., Arden Hills, MN (US)

( * ) Notice: Subject to any disclaimer, the term of this patent is extended or adjusted under 35 U.S.C. 154(b) by 0 days.

(21) Appl. No.: 09/909,148

(22) Filed: Jul. 19, 2001

(51) Int. Cl.[7] ............................................. A61B 5/0215
(52) U.S. Cl. ...................................... 600/301; 600/486
(58) Field of Search ................................. 600/301, 485, 600/486

(56) References Cited

U.S. PATENT DOCUMENTS 5,533,511 A * 7/1996 Kaspari et al. ............. 600/485
5,568,815 A * 10/1996 Raynes et al. .............. 600/485

* cited by examiner

*Primary Examiner*—Andrew M. Dolinar
(74) *Attorney, Agent, or Firm*—Kinney & Lange, P.A.

(57) ABSTRACT

An arterial line emulator interfaces a non-invasive blood pressure monitor with an invasive blood pressure monitor. The emulator receives pressure waveform signals from the non-invasive blood pressure monitor, and receives a transducer excitation voltage from the invasive blood pressure monitor. The emulator converts the pressure waveform signal from the non-invasive blood pressure monitor into an analog signal which is scaled as a function of the excitation voltage. The scaled analog pressure signal is supplied as an input to the invasive blood pressure monitor, and emulates the signal which would be received from a catheter-based blood pressure transducer.

18 Claims, 1 Drawing Sheet

ARTERIAL LINE EMULATOR

CROSS-REFERENCE TO RELATED APPLICATION(S)

None.

BACKGROUND OF THE INVENTION

The present invention relates to systems for measuring arterial blood pressure. In particular, the invention relates to a method and apparatus for interfacing a non-invasive blood pressure monitor with an invasive blood pressure monitor, so that pressure waveform information produced by the non-invasive blood pressure monitor is converted to a format which can be analyzed and displayed by the invasive blood pressure monitor.

Blood pressure has been typically measured by one of four basic methods: invasive, oscillometric, auscultatory and tonometric. The invasive method, otherwise known as an arterial line (A-Line), involves insertion of a needle into the artery. A transducer connected by a fluid column is used to determine exact arterial pressure. With proper instrumentation, systolic, mean and diastolic pressure may be determined. This method is difficult to set up, is expensive and involves medical risks. Set up of the invasive or A-line method poses problems. Resonance often occurs and causes significant errors. Also, if a blood clot forms on the end of the catheter, or the end of the catheter is located against the arterial wall, a large error may result. To eliminate or reduce these errors, the set up must be adjusted frequently. A skilled medical practitioner is required to insert the needle into the artery. This contributes to the expense of this method. Medical complications are also possible, such as infection or nerve damage.

The other methods of measuring blood pressure are non-invasive. The oscillometric method measures the amplitude of pressure oscillations in an inflated cuff. The cuff is placed against a cooperating artery of the patient and thereafter pressurized or inflated to a predetermined amount. The cuff is then deflated slowly and the pressure within the cuff is continually monitored. As the cuff is deflated, the pressure within the cuff exhibits a pressure versus time waveform. The waveform can be separated into two components, a decaying component and an oscillating component. The decaying component represents the mean of the cuff pressure while the oscillating component represents the cardiac cycle. The oscillating component is in the form of an envelope starting at zero when the cuff is inflated to a level beyond the patient's systolic blood pressure and then increasing to a peak value where the mean pressure of the cuff is equal to the patient's mean blood pressure. Once the envelope increases to a peak value, the envelope then decays as the cuff pressure continues to decrease.

Systolic blood pressure, mean blood pressure and diastolic blood pressure values can be obtained from the data obtained by monitoring the pressure within the cuff while the cuff is slowly deflated. The mean blood pressure value is the pressure on the decaying mean of the cuff pressure that corresponds in time to the peak of the envelope. Systolic blood pressure is generally estimated as the pressure on the decaying mean of the cuff prior to the peak of the envelope that corresponds in time to where the amplitude of the envelope is equal to a ratio of the peak amplitude. Generally, systolic blood pressure is the pressure on the decaying mean of the cuff prior to the peak of the envelope where the amplitude of the envelope is 0.57 to 0.45 of the peak amplitude. Similarly, diastolic blood pressure is the pressure on the decaying mean of the cuff after the peak of the envelope that corresponds in time to where the amplitude of the envelope is equal to a ratio of the peak amplitude. Generally, diastolic blood pressure is conventionally estimated as the pressure on the decaying mean of the cuff after the peak where the amplitude of the envelope is equal to 0.82 to 0.74 of the peak amplitude.

The auscultatory method also involves inflation of a cuff placed around a cooperating artery of the patient. Upon inflation of the cuff, the cuff is permitted to deflate. Systolic pressure is indicated when Korotkoff sounds begin o occur as the cuff is deflated. Diastolic pressure is indicated when the Korotkoff sounds become muffled or disappear. The auscultatory method can only be used to determine systolic and diastolic pressures.

Because both the oscillometric and the auscultatory methods require inflation of a cuff, performing frequent measurements is difficult. The frequency of measurement is limited by the time required to comfortably inflate the cuff and the time required to deflate the cuff as measurements are made. Because the cuff is inflated around a relatively large area surrounding the artery, inflation and deflation of the cuff is uncomfortable to the patient. As a result, the oscillometric and auscultatory methods are not suitable for long periods of repetitive use.

Both the oscillometric and auscultatory methods lack accuracy and consistency for determining systolic and diastolic pressure values. The oscillometric method applies an arbitrary ratio to determine systolic and diastolic pressure values. As a result, the oscillometric method does not produce blood pressure values that agree with the more direct and generally more accurate blood pressure values obtained from the A-line method. Furthermore, because the signal from the cuff is very low compared to the mean pressure of the cuff, a small amount of noise can cause a large change in results and result in inaccurate measured blood pressure values. Similarly, the auscultatory method requires a judgment to be made as to when the Korotkoff sounds start and when they stop. This detection is made when the Korotkoff sound is at its very lowest. As a result, the auscultatory method is subject to inaccuracies due to low signal-to-noise ratio.

The fourth method used to determine arterial blood pressure has been tonometry. The tonometric method typically involves a transducer including an array of pressure sensitive elements positioned over a superficial artery. Hold down forces are applied to the transducer so as to flatten the wall of the underlying artery without occluding the artery. The pressure sensitive elements in the array typically have at least one dimension smaller than the lumen of the underlying artery in which blood pressure is measured. The transducer is positioned such that at least one of the individual pressure sensitive elements is over at least a portion of the underlying artery. The output from one of the pressure sensitive elements is selected for monitoring blood pressure. The pressure measured by the selected pressure sensitive element is dependent upon the hold down pressure used to press the transducer against the skin of the patient. These tonometric systems measure a reference pressure directly from the wrist and correlate this with arterial pressure. However, because the ratio of pressure outside the artery to the pressure inside the artery, known as gain, must be known and constant, tonometric systems are not reliable. Furthermore, if a patient moves, recalibration of the tonometric system is required because the system may experience a change in gains. Because the accuracy of these tonometric systems depends upon the accurate positioning of the individual pressure sensitive element over the underlying artery, placement of the transducer is critical. Consequently, placement of the transducer with these tonometric systems is time-consuming and prone to error.

The oscillometric, auscultatory and tonometric methods measure and detect blood pressure by sensing force or displacement caused by blood pressure pulses as the underlying artery is compressed or flattened. The blood pressure is sensed by measuring forces exerted by blood pressure pulses in a direction perpendicular to the underlying artery. However, with these methods, the blood pressure pulse also exerts forces parallel to the underlying artery as the blood pressure pulses cross the edges of the sensor which is pressed against the skin overlying the underlying artery of the patient. In particular, with the oscillometric and the auscultatory methods, parallel forces are exerted on the edges or sides of the cuff With the tonometric method, parallel forces are exerted on the edges of the transducer. These parallel forces exerted upon the sensor by the blood pressure pulses create a pressure gradient across the pressure sensitive elements. This uneven pressure gradient creates at least two different pressures, one pressure at the edge of the pressure sensitive element and a second pressure directly beneath the pressure sensitive element. As a result, the oscillometric, auscultatory and tonometric methods produce inaccurate and inconsistent blood pressure measurements.

There has been a continuing need for devices which will measure blood pressure non-invasively, with accuracy comparable to invasive methods. Medwave, Inc. the assignee of the present invention, has developed non-invasive blood pressure measurement methods and devices which are described in the following United States patents, hereby incorporated by reference: U.S. Pat. No. 5,649,542 entitled CONTINUOUS NON-INVASIVE BLOOD PRESSURE MONITORING SYSTEM; U.S. Pat. No. 5,450,852 entitled CONTINUOUS NON-INVASIVE PRESSURE MONITORING SYSTEM; U.S. Pat. No. 5,640,964 entitled WRIST MOUNTED BLOOD PRESSURE SENSOR; U.S. Pat. No. 5,720,292 entitled BEAT ONSET DETECTOR; U.S. Pat. No. 5,738,103 entitled SEGMENTED ESTIMATION METHOD; U.S. Pat. No. 5,722,414 entitled CONTINUOUS NON-INVASIVE BLOOD PRESSURE MONITORING SYSTEM; U.S. Pat. No. 5,642,733 entitled BLOOD PRESSURE SENSOR LOCATOR; U.S. Pat. No. 5,797,850 entitled METHOD AND APPARATUS FOR CALCULATING BLOOD PRESSURE OF AN ARTERY; and U.S. Pat. No. 5,941,828 entitled HAND-HELD NON-INVASIVE BLOOD PRESSURE MEASUREMENT DEVICE.

As described in these patents, blood pressure is determined by sensing pressure waveform data derived from an artery. A pressure sensing device includes a sensing chamber with a diaphragm which is positioned over the artery. A transducer coupled to the sensing chamber senses pressure within the chamber. A flexible body conformable wall is located adjacent to (and preferably surrounding) the sensing chamber. The wall is isolated from the sensing chamber and applies force to the artery while preventing pressure in a direction generally parallel to the artery from being applied to the sensing chamber. As varying pressure is applied to the artery by the sensing chamber, pressure waveforms are sensed by the transducer to produce sensed pressure waveform data. The varying pressure may be applied automatically in a predetermined pattern, or may be applied manually.

The sensed pressure waveform data is analyzed to determine waveform parameters which relate to the shape of the sensed pressure waveforms. One or more blood pressure values are derived based upon the waveform parameters. The Medwave blood pressure measurement devices include both automated devices for continually monitoring blood pressure (such as in a hospital setting) and hand-held devices which can be used by a physician or nurse, or by a patient when desired. These devices represent an important improvement in the field of non-invasive blood pressure measurement.

The Medwave Vasotrac 205A is a non-invasive continual arterial blood pressure monitoring system. The Vasotrac 205A provides accurate blood pressure readings (systolic diastolic and mean pressure and pulse rate) every 15 heartbeats. It also displays blood pressure waveforms. Digital data, including digitized waveforms, can be output through a RS232 data port.

Despite the advantages offered by a non-invasive device such as the Medwave Vasotrac 205A, the A-line invasive systems represent the prevalent way in which continuous blood pressure monitoring is performed. The A-line monitors are designed to work with a catheter that is inserted into the patient's artery and has a blood pressure transducer for directly measuring arterial pressure. The invasive A-line blood pressure monitor provides a transducer excitation voltage to the transducer. The blood pressure signal received back from the transducer is a voltage that represents measured blood pressure. The pressure signal is a fraction of the excitation voltage. The invasive blood pressure monitor is calibrated to convert the pressure signal into measured blood pressure values and into or displayed blood pressure waveform based upon the relationship between the blood pressure signal and the excitation voltage.

BRIEF SUMMARY OF THE INVENTION

The present invention is a method and apparatus which permits a non-invasive blood pressure monitor to communicate with an invasive blood pressure monitor so that the blood pressure readings from the non-invasive blood pressure monitor can be used by the invasive blood pressure monitor in place of signals from an A-line blood pressure transducer. In the present invention, the non-invasive blood pressure monitor provides a signal representing the pressure waveform. That signal is converted into an analog signal representing the pressure waveform and is scaled as a function of an excitation voltage received from the invasive blood pressure monitor. The scaled analog pressure signal is supplied to the pressure signal input of the invasive blood pressure monitor.

BRIEF DESCRIPTION OF THE DRAWINGS

The FIG. 1 is a block diagram of the system which interfaces a non-invasive blood pressure monitor to an invasive blood pressure monitor.

DETAILED DESCRIPTION

Figure 1:
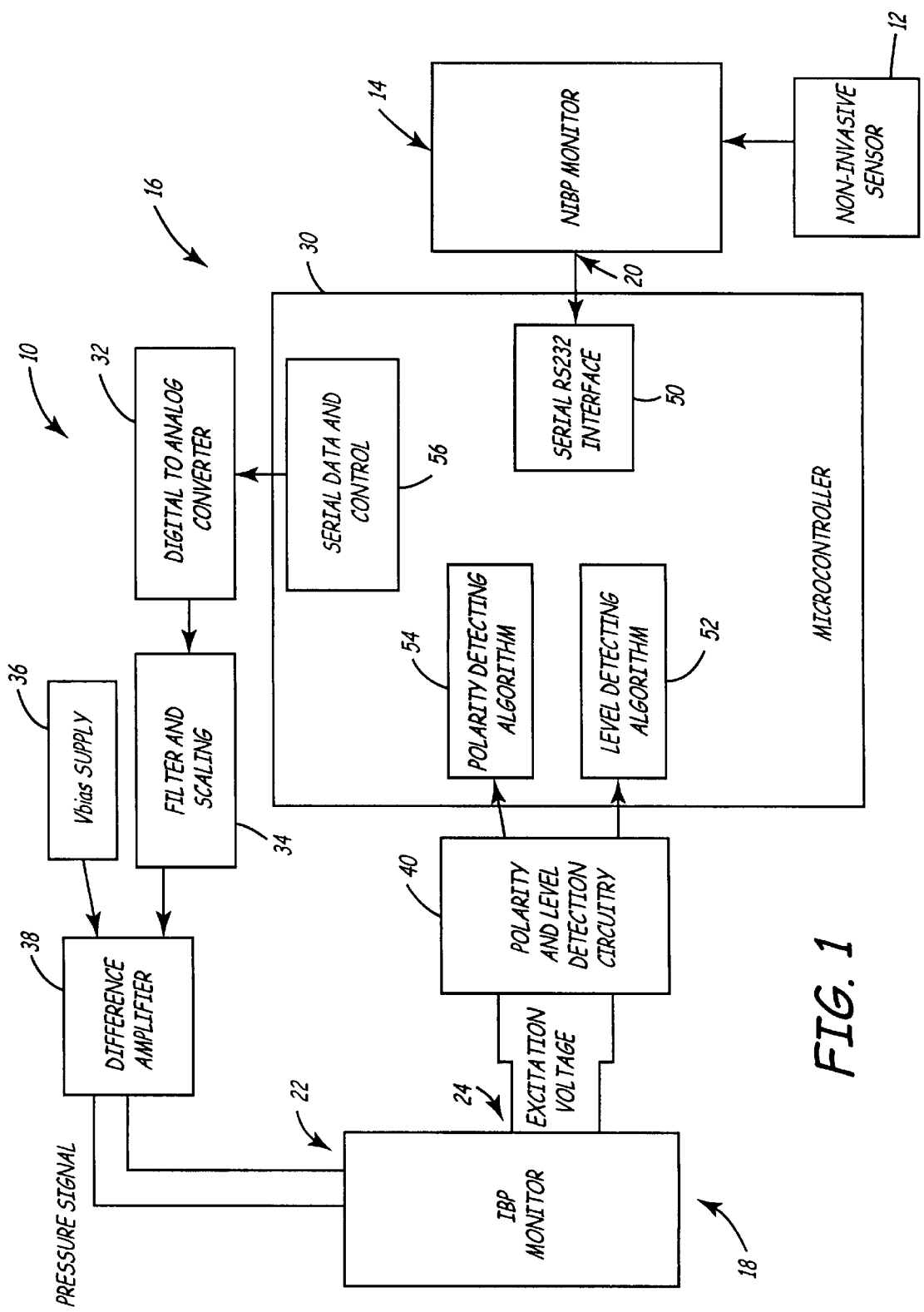

The FIGURE shows a blood pressure measurement system 10 including non-invasive sensor 12, non-invasive blood pressure (NIBP) monitor 14, arterial line emulator 16, and invasive blood pressure (IBP) monitor 18. Non-invasive sensor 12 makes a measurement of arterial blood pressure without requiring the insertion of a catheter into a patient's artery. The output of non-invasive sensor 12 is a pressure signal which is supplied to non-invasive blood pressure monitor 14.

Non-invasive blood pressure monitor 14 includes signal processing circuitry which derives blood pressure measurements such as systolic pressure, diastolic pressure, mean blood pressure, and pulse rate from the pressure signal supplied by non-invasive sensor 12. In addition, non-invasive blood pressure monitor 14 creates a blood pressure waveform showing the time varying change of blood pressure during a heartbeat.

In a preferred embodiment, non-invasive sensor 12 and NIBP monitor 14 are a Medwave Vasotrac 205A sensor and monitor, respectively. These devices are described in the previously mentioned patents and in patent application Ser. No. 09/721,216, filed Nov. 22, 2000, entitled WRIST MOUNTED BLOOD PRESSURE MEASUREMENT DEVICE. In this embodiment, non-invasive sensor 12 is connected through a cable to NIBP monitor 14. It is a wrist-mounted device which is placed over the radial artery of the patient. The pressure signal from non-invasive sensor 12 is an analog signal which is digitized by circuitry within monitor 14 to produce digitized blood pressure waveforms.

In this preferred embodiment, in which monitor 14 is the Vasotrac 205A monitor, blood pressure values, pulse rate, and arterial waveforms are displayed on monitor 14 and are updated approximately every 15 heartbeats. The data is also available in digital form through data port 20.

Emulator 16 takes digital data from data port 20 of NIBP monitor 14 and creates a pressure signal which is supplied as an input to invasive blood pressure (IBP) monitor 18. Emulator 16 connects to pressure signal input terminals 22 and excitation voltage output terminals 24 of invasive blood pressure monitor 18. Based upon the waveform data received from data port 20 of non-invasive blood pressure monitor 14, emulator 16 converts the digital waveform data to an analog signal, that is scaled based upon the excitation voltage from output terminals of IBP monitor 18, and provides the scaled analog pressure signal to input terminals 22 of IBP monitor 18.

IBP monitor 18 is any one of a wide variety of different arterial-line invasive blood pressure monitors. These monitors receive the analog pressure signal from a blood pressure transducer which is associated with the arterial-line catheter. The excitation voltage supplied from terminals 24 to the transducer powers the transducer and defines the maximum and minimum values of the transducer pressure signal. Typically, the pressure signal received by the IBP monitor 18 is a fraction of the excitation voltage, and is interpreted by IBP monitor 18 based upon that relationship.

Different IBP monitors 18 operate at different excitation voltages. In addition, the polarity of the excitation voltage differs from monitor to monitor. The purpose of emulator 16 is to interface NIBP monitor 14 with any one of a variety of different JBP monitors 18. This is done by sensing the excitation voltage from IBP monitor 18, and using that sensed voltage in producing the analog pressure signal which is supplied to the IBP monitor.

In the embodiment shown in the Figure, arterial line emulator 16 includes micro-controller 30, digital-to-analog converter 32, filter and scaling circuitry 34, Vbias supply 36, difference amplifier 38, and polarity and level detection circuitry 40.

Micro-controller 30 receives digital waveform data from NIBP monitor 14 at serial RS232 data interface 50. The data represents a series of digitized waveforms, and includes information indicating the correspondence of the pressure data to millimeters of mercury.

Micro-controller 30 scales the digital data representing the pressure waveform based upon the level of excitation voltage received from IBP monitor 18. Level detecting converter 52 is an algorithm, which provides micro-controller 30 with a digital value representing the magnitude of the excitation voltage.

Because the polarity of the excitation voltage can vary depending upon the manufacturer of IBP monitor 18, emulator 16 must determine the polarity of the excitation voltage. This is performed by polarity and level detection circuitry 40, which is connected to excitation voltage terminals 24 of IBP monitor 18. In a preferred embodiment, circuitry 40 is a two channel analog-to-digital circuit which provides inputs to level detecting algorithm 52 and polarity detecting converter 54 of micro-controller 30.

Based upon the polarity of the excitation voltage, micro-controller 30 provides a bipolar signal through digital-to-analog converter 32 either above or below Vbias, the nominal midpoint of the output voltage of digital-to-analog converter 32. Depending upon the difference between the digital-to-analog converter 32 output and Vbias, the polarity of the pressure signal supplied to terminals 22 of IBP monitor 18 can be reversed.

Based upon the detected level of excitation voltage, micro-controller 30 scales the digital data received from monitor 14. In other words, micro-controller 30 performs a gain control function based on the level of the excitation voltage. The scaled digital values will result in a pressure signal of the appropriate magnitude after the digital values are converted to analog values by converter 32 are scaled by filter and scaling circuitry 34, and are biased by Vbias supply 36 and amplified by difference amplifier 38. Serial data and control 56 of micro-controller 30 supplies the scaled digital data representing the pressure waveform to digital-to analog converter 32.

Filter and scaling circuit 34 smooths the analog signal received from converter 32 and scales the analog signal to the appropriate signal level for IBP monitor 18. The scaling performed by circuitry 34 uses a fixed scaling factor, in contrast to the variable scaling performed by micro-controller 30 as a function of the excitation voltage. Difference amplifier 38 compares the analog signal to the midpoint voltage bias Vbias and generates a signal of appropriate polarity. Micro-controller 30 causes the scaled digitized waveform to be sent by serial data and control 56 to digital-to-analog converter 32 repeatedly In other embodiments, additional data may be transferred in digital form from NIBP monitor 14 to micro-controller 30. In turn, digital information could also be provided from micro-controller 30 to a digital port of IBP monitor 18. This information may include, for example, the blood pressure values and heart rate which were determined by NIBP monitor 14. This would allow IBP monitor 18 to display waveforms, but use the blood pressure values and heart rate determined by NIBP monitor 14.

Alternatively, an analog signal from NIBP monitor 14 could be provided to emulator 16. The analog signal would then be scaled as a function of sensed excitation voltage and supplied to IBP monitor 18 with the proper magnitude and polarity.

Emulator 16 can be powered separately from monitors 14 and 18. In a preferred embodiment, power to emulator 16 is supplied by NIBP monitor 14 through the same RS232 cable which supplies digital data.

Although the present invention has been described with reference to preferred embodiments, workers skilled in the art will recognize that changes may be made in form and detail without departing from the spirit and scope of the invention.

What is claimed is:

1. A method of interfacing a non-invasive blood pressure monitor that produces digital data representing a non-invasively sensed blood pressure waveform with an invasive blood pressure monitor that provides an excitation voltage to an invasive blood pressure sensor and receives an analog pressure signal from the invasive blood pressure sensor at a pressure signal input, the method comprising:

converting the digital data to a scaled analog signal based upon the excitation voltage; and providing the scaled analog pressure signal to the pressure signal input invasive blood pressure monitor.

2. The method of claim 1 wherein converting the digital data comprises:

receiving the digital data from the non-invasive blood pressure monitor;

sensing the excitation voltage from the invasive blood pressure monitor;

scaling the digital data based upon the excitation voltage sensed; and converting the scaled digital data to the scaled analog pressure signal.

3. The method of claim 2 wherein converting the scaled digital data comprises:

performing a digital to analog conversion of the scaled digital data to produce a conventional signal; and signal processing the converted signal to produce the scaled analog pressure signal.

4. The method of claim 3 wherein the signal processing includes filtering the conventional signal.

5. The method of claim 3 wherein the signal processing includes scaling the converted signal.

6. The method of claim 2 and further comprising:

sensing polarity of the excitation voltage; and determining polarity of the scaled analog pressure signal based upon the sensed polarity of the excitation voltage.

7. A device for interfacing a non-invasive blood pressure monitor with an invasive blood pressure monitor, the device comprising:

means for receiving a blood pressure waveform signal from the non-invasive blood pressure monitor;

means for sensing an excitation voltage provided by the invasive blood pressure monitor; and means for providing to an input of the invasive blood pressure monitor a scaled analog pressure waveform signal which is a function of the blood pressure waveform signal received from the non-invasive blood pressure monitor and the excitation voltage sensed.

8. The device of claim 7 wherein the blood pressure waveform signal is digital data.

9. The device of claim 8 wherein the means for providing comprises:

means for scaling the digital data based upon the excitation voltage sensed; and means for converting the scaled digital data to the scaled analog pressure waveform signal.

10. The device of claim 9 wherein the means for converting comprises:

a digital-to-analog convertor for converting the scaled digital data to an analog signal; and filter and scaling circuitry for processing the analog signal to produce the scaled analog pressure waveform signal.

11. The device of claim 7 and further comprising:

means for sensing polarity of the excitation voltage; and means for controlling polarity of the scaled analog pressure waveform signal as a function of the sensed polarity of the excitation voltage.

12. A blood pressure monitoring system comprising:

a non-invasive blood pressure monitor that produces, at an output, a non-invasively sensed blood pressure waveform signal;

an invasive blood pressure monitor that displays blood pressure waveforms based upon an analog waveform signal received at an input from an invasive pressure sensor energized by an excitation voltage supplied by the invasive blood pressure monitor; and an emulator connected to the output of the non-invasive blood pressure monitor and the input of the invasive blood pressure monitor for providing to the input of the invasive pressure sensor an analog signal based upon the non-invasively sensed blood pressure waveform signal and the excitation voltage which emulates the analog waveform signal produced by an invasive pressure sensor.

13. The system of claim 12 wherein the emulator comprises:

means for receiving the non-invasively sensed signal from the output non-invasive blood pressure monitor;

means for sensing an excitation voltage provided by the invasive blood pressure; and means for providing the analog signal to the input of the invasive blood pressure monitor as a function of the non-invasively blood pressure waveform signal and the excitation voltage sensed.

14. The device of claim 13 wherein the blood pressure waveform signal is digital data.

15. The device of claim 12 wherein the means for providing comprises:

means for scaling the digital data based upon the excitation voltage sensed; and means for converting the scaled digital data to the analog signal.

16. A method of interfacing a non-invasive blood pressure monitor with an invasive blood pressure monitor, the method comprising:

receiving a blood pressure waveform signal from the non-invasive blood pressure monitor;

sensing an excitation voltage provided by the invasive blood pressure; and providing a scaled analog pressure waveform signal to an input of the invasive blood pressure monitor, the scaled analog pressure waveform signal being a function of the blood pressure waveform signal received from the non-invasive blood pressure monitor and the excitation voltage sensed.

17. The method of claim 16 wherein the blood pressure waveform signal is digital data.

18. A method of interfacing a non-invasive blood pressure monitor and an invasive blood pressure monitor, the method comprising:

receiving digital data representing a non-invasively sensed blood pressure waveform for the non-invasive blood pressure monitor;

sensing an excitation voltage supplied by the invasive blood pressure monitor;

producing an analog blood pressure waveform signal based upon the digital data, the analog blood pressure waveform signal having a period based upon the digital data and an amplitude based upon the digital data and an excitation voltage; and supplying the analog blood pressure waveform signal to an input of the invasive blood pressure monitor.

* * * * *